United States Patent [19]

Farin et al.

[11] Patent Number: 4,788,977
[45] Date of Patent: Dec. 6, 1988

[54] HIGH-FREQUENCY SURGICAL INSTRUMENT

[75] Inventors: Günter Farin, Tubingen-Hirschau; Peter Putz, Tubingen, both of Fed. Rep. of Germany

[73] Assignee: Erbe Elektromedizin GmbH, Tubingen, Fed. Rep. of Germany

[21] Appl. No.: 122,609

[22] Filed: Nov. 16, 1987

Related U.S. Application Data

[63] Continuation of Ser. No. 879,997, Jun. 30, 1986, abandoned.

[30] Foreign Application Priority Data

Jul. 4, 1985 [DE] Fed. Rep. of Germany ....... 3523871

[51] Int. Cl.$^4$ ............................................. A61B 17/39
[52] U.S. Cl. ................................. 128/303.13; 128/908
[58] Field of Search ....................... 128/303.13, 303.14, 128/303.17, 908

[56] References Cited

U.S. PATENT DOCUMENTS

| | | | |
|---|---|---|---|
| 4,122,854 | 10/1978 | Blackett | 128/303.13 |
| 4,231,372 | 11/1980 | Newton | 128/303.14 |
| 4,303,073 | 12/1981 | Archibald | 128/303.13 |
| 4,331,149 | 5/1982 | Gonser | 128/303.17 |

Primary Examiner—Lee S. Cohen
Attorney, Agent, or Firm—Nutter, McClennen & Fish

[57] ABSTRACT

Described is a safety circuit for a high-frequency surgical instrument for the monopolar cutting and coagulating of biological tissue, where the neutral electrode is high-frequency-grounded through a capacitor. The safety circuit monitors the low-frequency leakage current which flows through the capacitor against the ground potential and interrupts the electric connection between this capacitor and ground potential immediately when the low-frequency leakage current exceeds an adjustable limiting value. Simultaneously, an optical signal and an acoustical signal are activated.

17 Claims, 1 Drawing Sheet

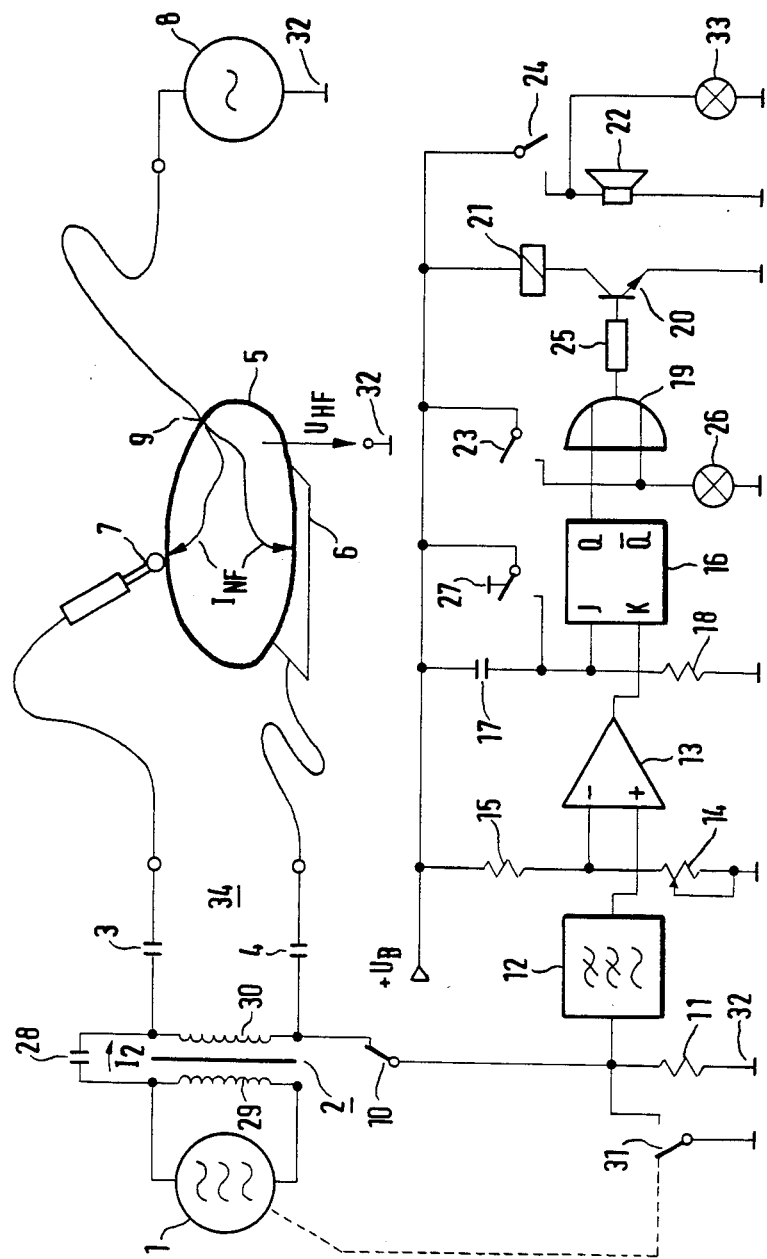

HIGH-FREQUENCY SURGICAL INSTRUMENT

This application is a continuation of an application of Gunter Farin and Peter Putz for HIGH-FREQUENCY SURGICAL INSTRUMENT filed June 30, 1986, and assigned application Ser. No. 06/879,997, now abandoned.

BACKGROUND OF THE INVENTION

1. Field of the Invention

The present invention relates to a high-frequency surgical instrument for the monopolar cutting and coagulating of biological tissues by means of a high-frequency electric current, whereby a neutral electrode is electrically connected across a capacitor against ground potential that the patient conducts the lowest possible high-frequency electric voltage against ground potential.

2. Discussion of the Prior Art

By definition, high-frequency surgical instruments used for monopolar surgical techniques are equipped in each case with an active electrode and an inactive, so-called neutral electrode. During the whole duration of the surgery, the neutral electrode is electrically connected to a large area of the skin of the patient, for example, to the thigh or the upper arm.

In principle, the neutral electrode can as a rule be electrically grounded as close as possible to the grounded operating table or may be insulated against ground potential. During the activation of the high-frequency surgical instrument, the grounded neutral electrode prevents the conduction of a high-frequency current through parts of the patient's body which are in contact with objects that are directly or capacitively grounded. Furthermore, electronic instruments, especially measuring and monitoring devices could be disturbed by the high-frequency alternating voltage which the patient would in that case conduct.

The grounding of the neutral electrode and related grounding of the patient create a danger that electric current from other grounded current sources, for example, defective electric appliances which simultaneously touch the patient in an electrically conductive manner, may flow through the patient and endanger him.

As a compromise between electrical grounding and the best possible insulation of the neutral electrode against ground potential, there are known high-frequency surgical instruments in which the neutral electrode is grounded across a capacitor. As a result, given suitable dimensioning of the capacitor, the neutral electrode lies, as regards the high-frequency voltage, practically at ground potential while low-frequency electric currents through the patient or the neutral electrode against ground potential remain sufficiently small. In the safety regulations for high-frequency surgical instruments VDE 0750, part 202, the capacity of this capacitor is limited to a maximum of 50 nF.

Regarding the safety of the patient with respect to risks from low-frequency electric currents, the recommendation of the IEC (International Electrotechnical Commission) Publication 601-1 subdivides electromedical instruments into three types according to the maximum permitted low-frequency leakage current, that is, the types B, BF and CF. In accordance with IEC 601-202 (identical with VDE 0750 part 202), high-frequency surgical instruments must conform to type BF or type CF. On instruments of type BF, the patient leakage current may reach a maximum of 0.1 mA on normal function and a maximum of 0.5 mA in the first error function. On instruments of the type CF, this leakage current may attain a maximum of only one tenth of the limiting values of the type BF. Furthermore, on instruments of the type CF, the leakage current which may flow through the patient into the high-frequency surgical instrument when the patient comes in contact with grounded line voltage must not exceed 0.05 mA.

SUMMARY OF THE INVENTION

It is an object of this invention so to construct a high-frequency surgical instrument in which the neutral electrode and thus the patient conducts a minimal high-frequency electric voltage against ground potential and that the low-frequency electric leakage currents which flow through the neutral electrode through the patient against ground potential do not endanger the patient.

This object is accomplished by equipping a known high-frequency surgical instrument with a capacitor of highest possible capacity, for example, 50 nF, between the neutral electrode and ground potential for reducing the high-frequency electric voltage between patient and ground potential. The instrument is additionally equipped according to the invention with a safety circuit which monitors the low-frequency electric leakage current through this capacitor and generates a warning signal and/or cuts off this capacitor from ground potential as soon as the low-frequency electric leakage current exceeds a defined limiting value.

BRIEF DESCRIPTION OF THE DRAWING

The invention is described in detail with the aid of the drawing, which is an exemplified embodiment of the safety circuit of the invention.

DETAILED DESCRIPTION OF THE PREFERRED EMBODIMENT

A high-frequency generator 1 is equipped with an isolating transformer 2, which isolates the range of application 34 of the high-frequency surgical instrument, which is in electrically conductive connection with the patient from the low-frequency operating voltage of the high-frequency generator 1. A low-frequency leakage current $I_2$, which can flow through the constructionally conditioned stray capacitance 28 from a primary winding 29 into a secondary winding 30, can without problems be so far reduced that it can practically be neglected.

A capacitor 3 between the secondary winding 30 of the transformer 2 and an active electrode 7 serves, as is well known, for the suppression of low-frequency electric currents caused by the non-linear dependence of the current from the voltage in electric arcs, which is unavoidable, especially in cutting.

A capacitor 4 is to represent, on the one hand, a very small impedance for the high-frequency electric current so that a high-frequency voltage $U_{HF}$ between patient 5 and ground potential 32 remains as small as possible and represent, on the other hand, the highest possible impedance for low-frequency electric current so that a low-frequency current $I_{NF}$ through the patient 5 remains as small as possible if, for example, a grounded low-frequency voltage source 8 contacts the patient 5 at a point 9. These two contrary demands have not been satisfactorily resolved in known high-frequency surgical instruments. In the high-frequency surgical instrument of this invention, the capacitor 4 is not, as is generally the case, directly electrically connected with ground potential 32, but through an automatic switch contact 10, which immediately opens when the low-frequency leakage current $I_{NF}$ exceeds a defined level. For this purpose, a current sensor is provided which consists, for example, of a resistance 11 and a voltage comparator 13. The low-frequency leakage current $I_{NF}$ generates across the resistance 11 a voltage which is proportional to the intensity of the leakage current $I_{NF}$. If this voltage exceeds a level established by a voltage divider 14, 15, then the voltage comparator 13 supplies a logical high-level which so sets a bistable flip-flop 16, e.g. a JK-flip-flop, at the input K that its output Q assumes a low-level which causes a transistor 20 to turn off and a relay 21 becomes currentless. Through this the switch contact 10, which is a contact of the relay 21, opens and thereby interrupts the electrically conductive connection between the capacitor 4 and ground potential 32. At the same time, a contact 24 of the relay 21 closes and cuts in an acoustic signal generator 22 and/or optical signal device 33 which warns the operating surgeon. This state is maintained until either an operating voltage $+U_B$ is cut out and again cut in or until a key 27 is actuated through which the JK-flip-flop 16 is so set that the output Q again assumes high-level or again switches via the OR-gate 19. Thus, the transistor 20 is turned on and the relay 21 again closes the contact 10 and opens again the contact 24, provided that the cause for the too high low-frequency leakage current $I_{NF}$ has previously been eliminated. Also, the definite setting of the JK-flip-flop 16 through the RC combination 17, 18 on each renewed switching-on of the operating voltage $+U_B$ ensures further that after each switching-on of the high-frequency surgical instrument, the contact 10 is closed and the contact 24 opened.

To prevent the voltage comparator 13 from being disturbed in its function by high-frequency voltages which could likewise arise at the resistance 11, there is provided a low-pass filter 12 which blocks both the operating frequency of the high-frequency generator 1 and also its harmonic frequencies.

The operating voltage $+U_B$ is advantageously drawn in known manner from an electronic voltage divider so that the threshold voltage of the voltage comparator 13 remains constant.

In further development of the invention, the safety circuitry of the invention is equipped with a contact 31 which automatically and time-synchronously with the activation of the high-frequency generator 1 closes and thus switches off the safety circuitry momentarily during the activation of the high-frequency generator 1.

This is of advantage when the limit for the low-frequency leakage current $I_{NF}$ has been set very low and transients in the high-frequency voltage at the resistance 11 cannot be sufficiently suppressed through the filter 12.

Another development of the invention consists in that the safety circuitry can be switched off through a switch 23, which simultaneously indicates an optical signal 26 showing that the safety circuit is disabled.

Among other things, an advantage of this safety circuit of the invention consists in that the low-frequency leakage currents which can flow through the patient 5 through the neutral electrode 6 and the capacitor 4 and/or through the patient 5 through the active electrode 7 and the capacitor 3 against ground potential, are recognized and prevented in time through automatic opening of the contact 10, regardless of whether this low-frequency leakage current is caused through an external low-frequency voltage source 8 or through an internal defect in the high-frequency surgical instrument, for example, an interruption of the protective wire of the high-frequency surgical instrument. Furthermore, the safety circuit of the invention of the high-frequency surgical instrument monitors whether the patient conducts dangerous low-frequency voltage against ground potential, regardless of what causes this voltage.

What is claimed as new and desired to be secured by Letters Patent of the United States is:

1. A high-frequency electrosurgical apparatus, said apparatus for producing a high-frequency current for the monopolar cutting or coagulating of biological tissue, said tissue being capable of conducting a low-frequency current which may be produced by one or more low-frequency current sources connected to said tissue or by said electrosurgical apparatus, said apparatus comprising:
   A. transformer means having a primary winding and a secondary winding, each of said primary and secondary windings having first and second teminals;
   B. high-frequency generator means coupled to the first and second terminals of said primary winding;
   C. active electrode means coupled to the first terminal of said secondary winding;
   D. neutral electrode means coupled to the second terminal of said secondary winding, at least one of said active electrode means and said neutral electrode means being coupled by a capacitor to its respective terminal;
   E. current sensing means, said sensing means being connected to provide a conductive path between said second terminal of said secondary winding and ground potential, said sensing means for monitoring said low-frequency current and producing a signal indicative of the magnitude thereof;
   F. first switch means, connected in said conductive path, said first switch means operating to alternately open and close said conductive path in response to a control signal; and
   G. control means, coupled to said sensing means, said control means for comparing the signal produced by the sensing means to a preselected reference signal and producing said control signal in response to the difference therebetween.

2. The high-frequency electrosurgical apparatus as in claim 1 wherein said control means further comprises a comparison means, said comparison means having first and second inputs and an output, said first input for receiving the signal produced by said sensing means, said second input for receiving said preselected reference signal, said output for producing said control signal.

3. The high-frequency electrosurgical apparatus as in claim 2 wherein said control means further comprises a filter means, said filter means being connected between said sensing means and said first input of said comparison means, said filter means operating to substantially block high frequency signals produced by said high-frequency generator means.

4. The high-frequency electrosurgical apparatus as in claim 2 wherein said control means further comprises an adjustale reference means, said adjustable reference means connected to said second input of said comparison means, thereby providing said preselected reference signal.

5. The high-frequency electrosurgical apparatus as in claim 4 wherein said adjustable reference means comprises a voltage divider.

6. The high-frequency electrosurgical apparatus as in claim 2 wherein said control means further comprises a bistable latch means, said latch means having first and second inputs and an output, said first input of said latch means connected to the output of said comparison means, said second input of said latch means for receiving an initialization signal, said output of said latch means coupled to said first switch means, said latch means operating to store said control signal.

7. The high-frequency electrosurgical apparatus as in claim 6 wherein said control means further comprises a relay means, said relay means being connected between the output of said latch means and said first switch means, said relay means being operative in response to said control signal to actuate said first switch means.

8. The high-frequency electrosurgical apparatus as in claim 7 wherein said control means further comprises a second switch means, said second switch means being coupled to said relay means, said second switch means being actuable to disable said relay means.

9. The high-frequency electrosurgical apparatus as in claim 8 wherein said second switch means comprises an optical indicator, said indicator being activated in response to the disabling of said relay means.

10. The high-frequency electrosurgical apparatus as in claim 6 wherein said latch means further comprises an initialization means connected to said second input of said latch means, said initialization means for providing said initialization signal, whereby, upon the activation of said electrosurgical apparatus, said first switch means is actuated, thereby closing said conductive path.

11. The high-frequency electrosurgical apparatus as in claim 6 or 10 wherein said control means further comprises a reset switch means, said reset switch means connected to said second input of said latch means, said reset switch means being operable to actuate said first switch means and close said conductive path.

12. The high-frequency electrosurgical apparatus as in claim 1 wherein a first capacitor is connected between said first terminal of said secondary winding and said active electrode means.

13. The high-frequency electrosurgical apparatus as in claim 12 wherein a second capacitor is connected between the second terminal of said secondary winding and said neutral electrode means.

14. The high-frequency electrosurgical apparatus as in claim 1 wherein a first capacitor is connected between the second terminal of said secondary winding and said neutral electrode means.

15. The high-frequency electrosurgical apparatus as in claim 1 wherein the control means further comprises an optical indicator, said optical indicator being activated in response to the opening of said conductive path.

16. The high-frequency electrosurgical apparatus as in claim 1 or 15 wherein the control means further comprises an acoustical indicator, said acoustical indicator being activated in response to the opening of said conductive path.

17. The high-frequency electrosurgical apparatus as in claim 1 wherein said control means further comprises disabling means, said disabling means operating to automatically disable said control means during the activation of said high-frequency generator means and to otherwise enable said control means.

* * * * *